Figure 1:
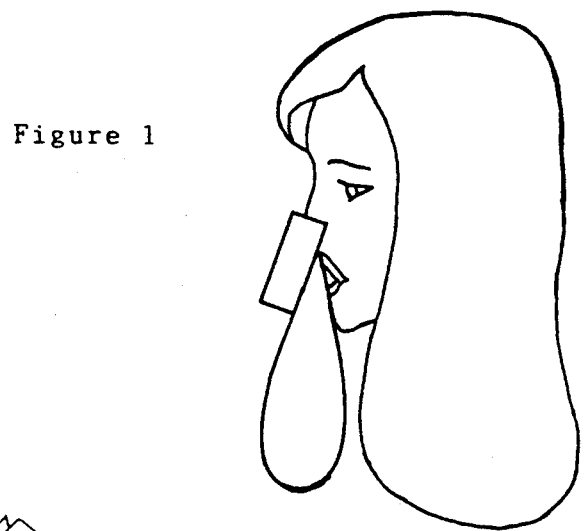

United States Patent [19]

Hepburn

[11] Patent Number: 5,154,167
[45] Date of Patent: Oct. 13, 1992

[54] LUNG AND CHEST EXERCISER AND DEVELOPER

[76] Inventor: Christopher H. Hepburn, 4 Lithos Road, London NW3 6EF, England

[21] Appl. No.: 509,889

[22] Filed: Apr. 16, 1990

[51] Int. Cl.$^5$ .......... A62B 7/00; A62B 9/00; A62B 18/00; A63B 23/00

[52] U.S. Cl. .......... 128/200.24; 128/205.17; 128/205.13; 128/914; 482/13

[58] Field of Search .......... 128/200.24, 204.18, 128/205.11, 205.13, 205.14, 205.17, 914, 205.24; 272/99

[56] References Cited

U.S. PATENT DOCUMENTS

| 2,292,474 | 8/1942 | Paxton | 128/200.24 |
|---|---|---|---|
| 2,843,119 | 7/1958 | Glasser | 128/205.17 |
| 3,949,984 | 4/1976 | Navora | 272/99 |
| 4,192,301 | 3/1980 | Hardwick | 128/205.17 |
| 4,207,884 | 6/1980 | Isaacson | 128/200.24 |
| 4,275,722 | 6/1981 | Sorensen | 128/200.24 |
| 4,301,810 | 11/1981 | Belman | 128/200.24 |
| 4,854,574 | 8/1989 | Larsen et al. | 128/200.24 |

FOREIGN PATENT DOCUMENTS

| 840168 | 4/1970 | Canada | 128/205.17 |
|---|---|---|---|
| 0143208 | 5/1985 | European Pat. Off. . | |
| 2599629 | 12/1987 | France | 128/200.24 |
| 571867 | 1/1976 | Switzerland | 128/200.24 |
| 1179972 | 9/1985 | U.S.S.R. | 128/200.24 |
| 2113555 | 8/1983 | United Kingdom . | |

*Primary Examiner*—Edgar S. Burr
*Assistant Examiner*—Kimberly L. Asher

[57] ABSTRACT

A lung and chest exerciser that arranges for some of the air expired from the lungs on an outbreath to be collected and then to be breathed back into the lungs on the next inbreath, together with some fresh air. By so arranging, the lungs have to open deeper or more often to receive an equivalent amount of fresh air. An embodiment of the invention may have a body, a collector bag, an adjustment slider, a filter and a nose-piece. The exerciser directly develops the lungs and the respiratory muscles and indirectly exercises the heart thereby affecting the body's metabolism, circulation and relaxation level.

9 Claims, 3 Drawing Sheets

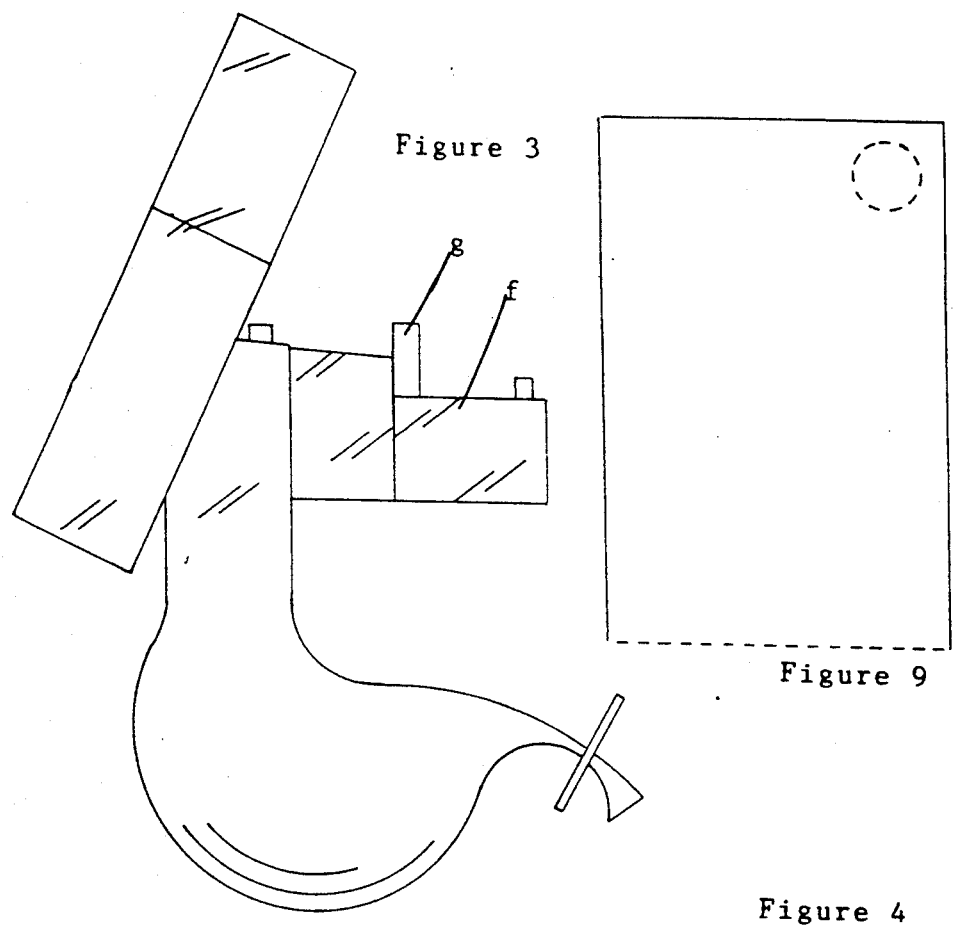
Figure 3
Figure 9
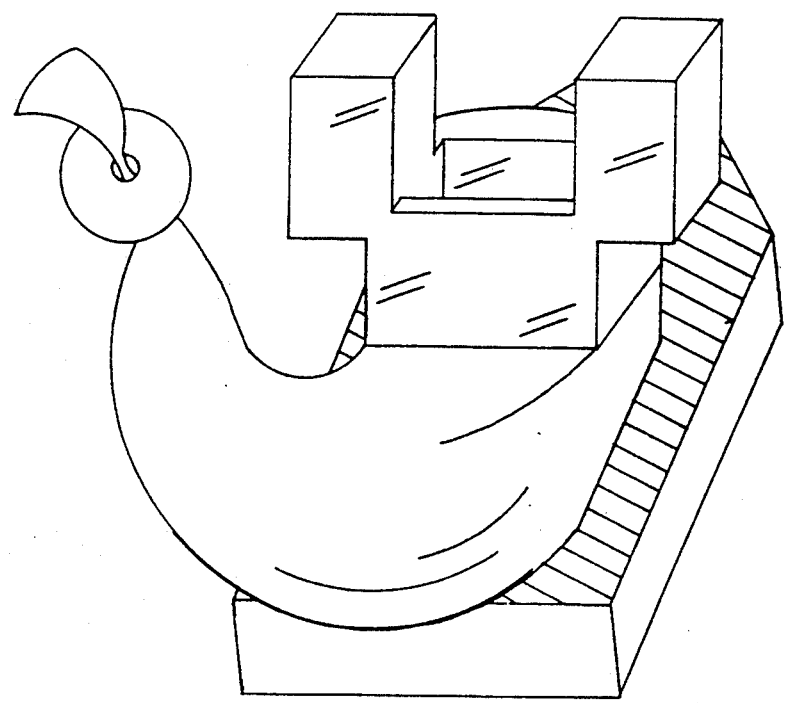
Figure 4

LUNG AND CHEST EXERCISER AND DEVELOPER

This invention relates to a device for the exercise and development of the lungs and chest. The device will be referred to as a "Lung Exerciser".

There are currently devices available that indirectly exercise the lungs by exercising some separate bodily activity, such as an exercise bicycle or a rolling road. There are devices for exercising the chest muscles, such as chest expander springs and free weights. This device exercises the lungs, and the chest and stomach muscles directly subsequently exercises the heart. The Lung Exerciser also affects the blood's CO2 level which is of health and medical use.

The aim of the present invention is to provide a device that arranges for some of the air expired from the lungs on an outbreath to be collected and then to be breathed back into the lungs on the next inbreath together with some fresh air. By so arranging, to receive a mix of expired and fresh air the lungs have to open deeper or more often to receive an equivalent amount of fresh air.

The device comprises a bag having a mouthpiece through which air can be inhaled from the bag and exhaled to the bag, and valve means through which the mouthpiece is connected to atmosphere, the valve means providing a resistance to air flow, whereby appreciable quantities of fresh air will only be drawn through the valve means from the atmoshphere when the differential pressure on the two sides of the valve means is sufficiently high.

In the embodiment set out later the lungs may breathe back in all the collected expired air before breathing in fresh air, causing the lungs to open deeper or, on a different setting, the lungs may breathe in a mixture of expired air and fresh air thus allowing the lungs to open more frequently.

On a suitable setting a person can use the device for extended periods of time without adjustment and without feeling breathless. An embodiment of the invention will now be described solely by way of example and with reference to the accompanying figures.

Figure 2:
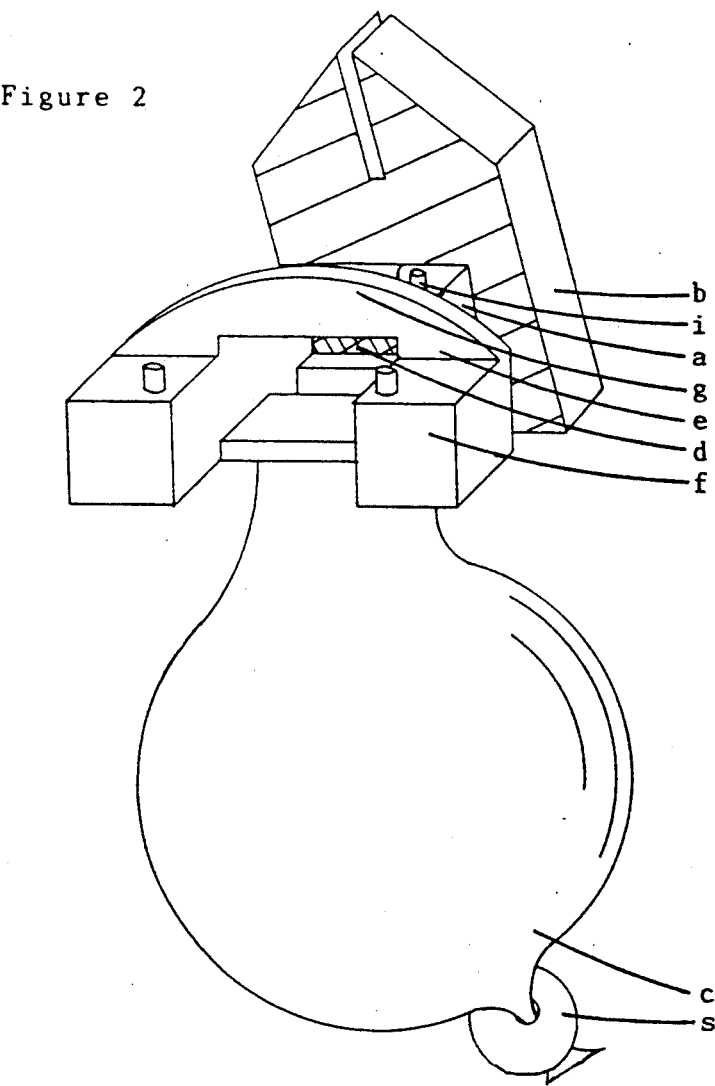
Figure 5:
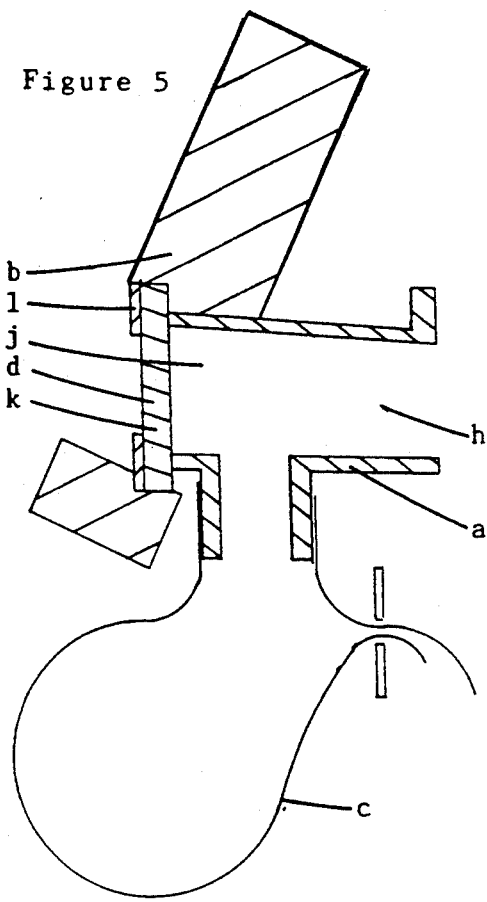
Figure 6:
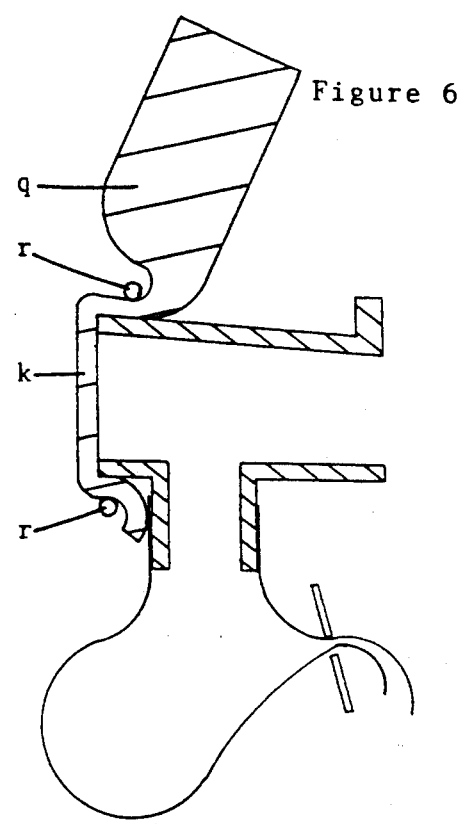
Figure 7:
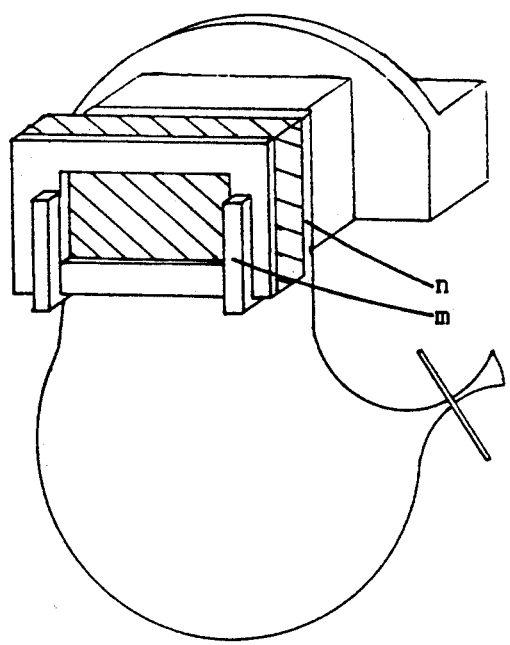
Figure 8:
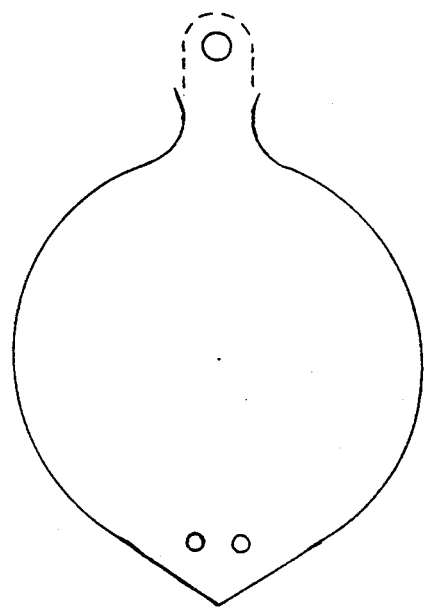

FIG. 1 shows a person using a lung exerciser.
FIG. 2 shows a general view of a lung exerciser.
FIG. 3 shows a side view.
FIG. 4 shows an underview.
FIG. 5 shows a cross-section taken along the central vertical axis.
FIG. 6: A cross-sectional viewing showing that the nose-piece and filter being made of a single piece of material.
FIG. 7: A viewing of the device with the nose-piece removed.
FIG. 8: A template of the back shape.
FIG. 9: A template to the back shape.

The Lung Exerciser consists of a body (a), a nose piece (b), a collector bag (c) and a filter valve (d).

The body (a) has a mouthpiece (e) shaped rather like a snorkel tube's mouthpiece with lugs (f) for the person's teeth to grip and a protruding rim (g) for the person's lips to go around. For the device to operate it is required for a person's lips to seal around the body. The mouthpiece has an airway (h). This may have a cross-sectional area of at least 1 cm$^2$. The mouthpiece may have a protruding lip to prevent saliva trickling into the airway.

The airway leads into a collector bag (c). This bag is airtight. It is inflated by the person breathing down the airway. The bag may be a plastic bag. On it may be printed advice, volume calibrations or a decorative pattern. The collector bag may be attached to the body by means of a rubber band or by sliding over part of the body. (n, FIG. 7) or by fixing onto hooks (i, FIG. 2). FIG. 8 shows the template of a collector bag suitable for use with fixing hooks and FIG. 9 shows the template of a collector bag suitable for looping over the body. The edges of the template are sealed except for where the outline is a dotted line where the two sides of the bag are left open. The bag may be of a design such that its volume can be altered by attaching various amounts of the bag to the body.

Connected to the collector bag is another airway (j) which leads to the filter and valve (d). This airway may be part of the body. The filter cleans air that travels through the airway. The valve may be a constriction in the air passage which may be variable or may be the resistance due to the filter material.

In the embodiment shown the valve consists of filter material (k) which is held in place by washer (1) which fit behind lugs (m, FIG. 7).

Filter material may be chosen such that with a single thickness the air resistance is such that on an inbreath some air is drawn through the filter at the same time as air is drawn up from the collector bag providing a blend of fresh and expired air and such that with a double thickness of filter material the air resistance is such that on an inbreath all the air in the collector bag is breathed in before air is drawn through the filter. Integral to the body (a) or attached to it is a nosepiece (b). This has two protuberances that rest on either side of the person's nostrils.

The nosepiece restricts flow of air up or down the nostrils either by holding the nostrils closed or by blocking them. The material of the nosepiece may be selected so that only light pressure is placed on the nostrils. Expanded polyurethane foam is a suitable such material. By using a light pressure a person may, if they wish, override the nose-piece and breathe air up or down their nose. Typically this may be done by blocking the air passage (h) with the person's tongue and taking a firm breath. The airway from the collector bag can be closed by taking a sharp inbreath which causes the top of the collector bag to close against itself and the entrance to the airway. When this airway is closed a continuing inbreath causes fresh air to be drawn through the filter.

The nosepiece may have a fabric cover for extra comfort.

The nosepiece may be attached to the body on lugs protruding from the body or by using a rubber band or by going around the body. FIG. 7 shows the Lung Exerciser with the nosepiece removed. The nosepiece and filter may be made from one piece of foam. Such an arrangement is shown in FIG. 6. This shows a cross-sectional view along a vertical axis. The piece of foam (q) which makes up the nosepiece (b) and provides the filter material (k) is held in place by the clip (r).

It is appreciated that the embodiment of the invention described above with reference to the accompanying Figures has been given by way of example only and that modification may be effected.

For example instead of having a snorkel type mouthpiece gripped by the teeth a face mask may be used similar to ones used for gas masks or for dust masks.

These masks: may have speak-through panels. The snorkel type mouthpiece may have lugs or clamps that locate onto a person's teeth. A person might then be able to open their mouth freely with the Lung Exerciser staying in place. The exerciser may fit around a person's nose, so that they breathe through their nose.

The exerciser may be used without the nosepiece.

The collector bag may be of a material or have corrugations moulded into it so that it is silent or so that it does not close up on itself during use. On the collector bag may be used a slider (s) to alter the useable volume quickly. Attached to the slider may be a small plastic bag into which the unused part of the collector bag may be stored.

Attached to the exerciser may be various meters. These may measure the volume of air expired, measure the oxygen or carbon dioxide content of the inhaled or exhaled air, measure a person's pulse or blood pressure or measure their temperature or their blood sugar levels. Attached to these meters may be alarm warnings and failsafe mechanisms.

There may be a means of administering pharmaceuticals to the air collected.

A counting mechanism could be fitted to count the number of breaths.

The body (a) may have a cushioned pad to rest against a person's chin.

The collector bag may be partly or wholly constructed of a material that is air permeable. By using such material the air filter and valve may be dispensed with. The body may be shaped to keep part of the collector bag extended on an inbreath. The body may be so constructed such that the filter is an integral part of the body.

The Lung Exerciser may be adapted for animals, in particular a face mask may be produced for race horses or for greyhounds.

The Lung Exerciser is especially advantageous in the way that it affects the lungs, respiratory muscles, the functioning of the heart and circulation, its effect on the blood CO2 level which is known to cause relaxation, of increasing metabolism, of affecting cholesterol levels, of changing blood pressures, of how it has a massage-like effect in reducing bodily tensions, of promoting tissue regrowth, its ease of usage, its adaptability and economic outlay.

I claim:

1. A respiratory rebreathing device comprising a mouthpiece, a collector bag having a top and a bottom portion for receiving exhaled air from a user, an inlet for permitting inhalation of atmospheric air by the user, and an air passage connecting said mouthpiece, said bag, and said inlet; means for variably restricting said inlet, said restricting means allowing entry of appreciable quantities of atmospheric air only in response to at least a predetermined level of inhalation force by a user, said restricting means not allowing entry of appreciable amounts of atmospheric air in response to inhalation attempts below said predetermined level, wherein a weak inhalation effort by a user results in the inhalation of mainly previously exhaled air from said bag, and an increased inhalation attempt at least of a force to meet said predetermined level results in the inhalation of increased amounts of atmospheric air; and means for permitting only inhalation of atmospheric air comprising entrance means on said bag, said entrance means preventing inhalation of previously exhaled gas by closing together in response to a sharp inbreath by a user, wherein with said entrance means closed, a continuing inbreath by a user causes atmospheric air to be inhaled by a user through said inlet.

2. The device of claim 1 wherein said means for restricting said inlet comprises a filter having a resistance to air flow, said resistance acting as a valve.

3. The device of claim 1 wherein said means for restricting said inlet comprises a filter and a valve, said valve being in the form of a constriction in said inlet.

4. The device of claim 1 wherein said air passage has a crossection of at least 1 $cm_2$.

5. The device of claim 1 wherein said mouthpiece further comprises a nosepiece for restricting air flow through a user's nose.

6. The device of claim 1 wherein said bag contains a volume, and further comprises means for varying said volume.

7. The device of claim 6 wherein said means for varying said volume comprises a slider.

8. The device of claim 1 further comprising a face mask.

9. The device of claim 1 wherein said mouthpiece comprises means for gripping by a user's teeth.

* * * * *